(12) United States Patent
Carroll

(10) Patent No.: US 7,486,984 B2
(45) Date of Patent: Feb. 3, 2009

(54) SYSTEM AND METHOD FOR MONOCHROMATIC X-RAY BEAM THERAPY

(75) Inventor: Frank E. Carroll, Nashville, TN (US)

(73) Assignee: MXISystems, Inc., Fairview, TN (US)

( * ) Notice: Subject to any disclaimer, the term of this patent is extended or adjusted under 35 U.S.C. 154(b) by 895 days.

(21) Appl. No.: 10/848,151

(22) Filed: May 19, 2004

(65) Prior Publication Data
US 2005/0259787 A1 Nov. 24, 2005

(51) Int. Cl.
A61B 6/00 (2006.01)
H01J 35/14 (2006.01)

(52) U.S. Cl. .............. 600/436; 378/138; 378/119; 378/65; 600/407; 600/427

(58) Field of Classification Search .............. 600/436, 600/411, 161, 407, 427; 514/23; 378/119, 378/417, 138, 65
See application file for complete search history.

(56) References Cited

U.S. PATENT DOCUMENTS

| | | | |
|---|---|---|---|
| 3,381,127 A | 4/1968 | Monroe |
| 3,576,997 A | 5/1971 | Slavin |
| 3,772,522 A | 11/1973 | Hammond et al. |
| 3,777,156 A | 12/1973 | Hammond et al. |
| 4,010,370 A | 3/1977 | LeMay |
| 4,037,920 A | 7/1977 | Runciman et al. |
| 4,082,416 A | 4/1978 | Runciman et al. |
| 4,082,417 A | 4/1978 | Runciman et al. |
| 4,118,099 A | 10/1978 | Weiss et al. |
| 4,132,654 A | 1/1979 | Braun |
| 4,144,457 A | 3/1979 | Albert |
| 4,149,076 A | 4/1979 | Albert |
| 4,179,100 A | 12/1979 | Sashin et al. |
| 4,203,034 A | 5/1980 | Carroll, Jr. |
| 4,210,810 A | 7/1980 | Berry et al. |
| 4,298,800 A | 11/1981 | Goldman |
| 4,311,389 A | 1/1982 | Fay et al. |
| 4,342,914 A | 8/1982 | Bjorkholm |
| 4,441,809 A | 4/1984 | Dudley et al. |
| 4,598,415 A | 7/1986 | Luccio et al. |
| 4,599,741 A | 7/1986 | Wittry |
| 4,809,309 A | 2/1989 | Beekmans |

(Continued)

OTHER PUBLICATIONS

Biston, et al., *Cure of Fisher Rats Bearing Radioresistant F98 Glioma Treated with cis-Platinum and Irradiated with Monochromatic Synchrotron X-Rays*, Cancer Research 64, 2317-2323, Apr. 1, 2004.

(Continued)

*Primary Examiner*—Eric F Winakur
*Assistant Examiner*—Lawrence N Laryea
(74) *Attorney, Agent, or Firm*—Cooley Godward Kronish LLP

(57) ABSTRACT

In embodiments of the invention, a radiosensitizer or other agent is relatively uniformly accumulated in the cells of a tumor. An external monochromatic x-ray beam, which is tuned to a predetermined energy level associated with k-edge effects in the agent, is then directed to the tumor. The monochromatic x-ray beam activates the release of additional localized radiation from the agent. The additional radiation destroys the DNA of at least some tumor cells, making those tumor cells incapable of reproduction and repair. In embodiments of the invention, a single monochromatic x-ray beam source is used for both imaging and radiotherapy.

34 Claims, 4 Drawing Sheets

U.S. PATENT DOCUMENTS

| | | |
|---|---|---|
| 4,953,188 A | 8/1990 | Siegel et al. |
| 4,958,363 A | 9/1990 | Nelson et al. |
| 4,975,917 A | 12/1990 | Villa |
| 5,011,245 A | 4/1991 | Gibbs |
| 5,125,019 A | 6/1992 | Evain et al. |
| 5,132,997 A | 7/1992 | Kojima et al. |
| 5,138,642 A | 8/1992 | McCroskey et al. |
| 5,227,733 A | 7/1993 | Yamada |
| 5,245,648 A | 9/1993 | Kinney et al. |
| 5,247,562 A | 9/1993 | Steinbach |
| 5,263,073 A | 11/1993 | Feldman |
| 5,268,951 A | 12/1993 | Flamholz et al. |
| 5,268,954 A | 12/1993 | Middleton |
| 5,315,375 A | 5/1994 | Allen |
| 5,353,291 A | 10/1994 | Sprangle et al. |
| 5,479,017 A | 12/1995 | Yamada et al. |
| 5,495,515 A | 2/1996 | Imasaki |
| 5,509,043 A | 4/1996 | Van Der Sluis |
| 5,541,944 A | 7/1996 | Neil |
| 5,602,894 A | 2/1997 | Bardash |
| 5,604,782 A | 2/1997 | Cash, Jr. |
| 5,628,314 A | 5/1997 | Kumagai |
| 5,781,606 A | 7/1998 | Dobbs et al. |
| 5,805,620 A | 9/1998 | Liu et al. |
| 5,815,517 A | 9/1998 | Ikegami |
| 5,825,847 A | 10/1998 | Ruth et al. |
| 5,850,425 A | 12/1998 | Wilkins |
| 5,881,126 A | 3/1999 | Momose |
| 5,930,325 A | 7/1999 | Momose |
| 5,930,331 A | 7/1999 | Rentzepis et al. |
| 6,023,496 A | 2/2000 | Kuwabara |
| 6,035,015 A | 3/2000 | Ruth et al. |
| 6,108,397 A | 8/2000 | Cash, Jr. |
| 6,128,364 A | 10/2000 | Niemann |
| 6,195,410 B1 | 2/2001 | Cash, Jr. |
| 6,226,354 B1 | 5/2001 | Haversat |
| 6,327,335 B1 | 12/2001 | Carroll |
| 6,332,017 B1 | 12/2001 | Carroll et al. |
| 6,459,766 B1 | 10/2002 | Srinivasan-Rao |
| 6,687,333 B2 | 2/2004 | Carroll et al. |
| 6,693,931 B1 | 2/2004 | Mendenhall et al. |
| 7,221,733 B1 | 5/2007 | Takai et al. |
| 2005/0080019 A1* | 4/2005 | Wang .......................... 514/23 |

OTHER PUBLICATIONS

Pignol, M.D., Ph.D., et al., *Clinical Significance of Atomic Inner Shell Ionization (ISI) and auger cascade for Radiosensitization Using IudR, BudR, Platinum Salts, or Gadolinium Porphyrin Compounds*, Int. J. Radiation Oncology Biol. Phys., vol. 55, No. 4, pp. 1082-1091, 2003.

Karnas, et al., *Optimal Photon Energies for IudR K-edge Radiosensitization with Filtered X-ray and Radioisotope Sources*, Phys. Med. Biol. 44 (1999) 2537-2549, Printed in the UK.

Kinsella, et al., *Preclinical Toxicity and Efficacy Study of a 14-day Schedule of Oral 5-Iodo-2pyrimidinone-2'-deoxyribose as a Prodrug for 5-Iodo-2'-Glioblastoma Xenografts*, Clinical Cancer Research, vol. 6, 1468-1475, Apr. 2000.

Carroll, *Tunable, Monochromatic X-Rays: An Enabling Technology for Molecular/Cellular Imaging and Therapy*, Journal of Cellular Biochemistry 90:502-508 (2003).

* cited by examiner

SYSTEM AND METHOD FOR MONOCHROMATIC X-RAY BEAM THERAPY

CROSS-REFERENCE TO RELATED APPLICATIONS

The disclosures of U.S. Pat. Nos. 6,332,017, 6,687,333 and 6,693,931 are hereby incorporated by reference in their entirety.

BACKGROUND

The invention relates generally to the field of medical science. In particular, but not by way of limitation, the invention relates to a system and method for performing radiotherapy using monochromatic x-ray beams.

Systems and methods are known for performing radiotherapy. For instance, conventional cancer treatments use radiation therapy to deliver a lethal dose of radiation to cancerous tumor tissues and/or the related margin tissue. Radiation therapy can be an attractive alternative to surgery because radiation therapy can be entirely non-invasive. Radiation therapy can be divided into two categories, external beam and brachytherapy. External beam is radiation originating outside the body and aimed at the tumor or object of treatment; brachytherapy is radiation treatment where the radiation source is placed within or adjacent to the site to be treated.

Known methods for delivering external beam radiation have various disadvantages. For example, a significant disadvantage of conventional external beam radiotherapy is the undesirable effect on tissue in non-targeted areas. In an effort to minimize this problem, radiation can be introduced to the body at several different angles—delivering a relatively small amount in each of multiple treatments, with a lethal dose accumulating over many days at the central point of all the projections, the targeted tumor and/or related margin tissue.

Because a tumor presents different profiles and thickness at each angle, methods have been developed to vary the intensity of the beam radiation. This intensity difference can be achieved with longer exposure times and with different radiation intensities. Varying the intensity of the beam at each projection is often referred to as IMRT (Intensity Modulated Radiation Therapy). The use of IMRT has expanded rapidly, adding to the expense and complexity of the delivery systems and the planning of the treatment. Planning the radiation treatment regimen for a patient is a complex process where the numerous angles, beam shape, beam intensity, and number of treatments (fractions) are considered to calculate the minimum dose to the target tissue and the maximum dose allowed to the areas to be spared.

The difficulty of treating a patient in this manner is further complicated by difficulties in assuring that the target tissue being treated is precisely in the path of the radiation beam. This is because the apparatus used for imaging the target tumor or margin tissue is not the same apparatus used for treatment. Patient movements between imaging and treatment can thus change the position of the target tissue with respect to marks placed on the skin, or with respect to bony structures in the patient. Moreover, the size and location of the target tissue can and does change during a course of a treatment that lasts for several weeks. All of these factors contribute to the difficulty in aligning the external radiation beam with the target tissue.

Even where external beam radiation is on target, known systems and methods require high doses of radiation (typically 60-80 Gy) using very high energy x-ray photons in the 4-25 MeV range. The result is a debilitating, lengthy, and difficult process for the patient, commonly causing radiation sickness and/or other temporary or permanent side effects. Moreover, because of the effect of high doses of radiation on neighboring non-target tissue, known radiation treatment cannot be used where the target tissue is proximate to deep organs. For example, use of radiotherapy for treating head and neck tumors, or for treating recurrent skin tumors of the scalp and face, is suboptimal due to the high risk of injury to neural and brain tissues.

Therefore, a need exists for a system and method that simplifies and improves the accuracy of targeting external beam radiation. In addition, a system and method is needed that reduces the amount of external beam radiation energy that is applied to destroy target tissues.

SUMMARY OF THE INVENTION

Embodiments of the invention provide a method including: accumulating an agent in a target tissue; and applying an external substantially monochromatic x-ray beam to the target tissue, the external substantially monochromatic x-ray beam being tuned approximately to a binding energy level of an electron shell in an atom of the agent. Slightly higher energy levels may also be used.

Other embodiments of the invention provide a method for performing diagnosis and therapy, including: accumulating iodine (or Gadolinium, or Platinum, or other agent) in the DNA of a target tissue; tuning the substantially monochromatic x-ray beam to approximately 33.2 keV at a location of the target tissue; and externally applying the tuned substantially monochromatic x-ray beam to the target tissue, a first portion of the DNA of the target tissue breaking from a second portion of the DNA of the target tissue in response to the applying.

Other embodiments of the invention provide a method including: delivering a first agent in a target tissue; imaging the target tissue based on a first external substantially monochromatic x-ray beam; destroying cells of the target tissue based on a second external substantially monochromatic x-ray beam.

Exemplary embodiments of the invention shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

BRIEF DESCRIPTION OF THE DRAWINGS

Embodiments of the invention are described with reference to the following drawings.

DETAILED DESCRIPTION

In embodiments of the invention, a radiosensitizer or other agent is somewhat uniformly accumulated in the cells of a tumor. An external monochromatic x-ray beam, which is tuned to a predetermined energy level associated with k-edge effects in the agent, is then directed to the tumor. The monochromatic x-ray beam activates the release of additional radiation from the agent. The additional radiation destroys the DNA of at least some tumor cells, making those tumor cells incapable of reproduction and repair (effectively destroying the cells). In embodiments of the invention, a single monochromatic x-ray beam source is used for both imaging and performing radiotherapy.

Advantageously, the additional radiation released from the agent remains substantially proximate to the tumor cells, protecting non-cancerous tissue. In addition, because the agent is relatively uniformly accumulated in the tumor, thicker portions of the tumor will be subjected to relatively higher levels of additional radiation, rendering the treatment inherently conformal in intensity without the need to adjust the intensity of the external beam. Further, where a single monochromatic x-ray beam source is used for both imaging and radiotherapy, alignment errors caused by patient re-positioning are significantly reduced. Moreover, because the mono-chromatic x-ray beam is merely an activator, it is administered at a much lower level of intensity compared to conventional external beam therapy. The invention therefore enables the application of radiotherapy to lesions heretofore too proximal to organs.

This section provides an overview of diagnostic and therapeutic processes, provides more detailed description of each, suggests alternative embodiments, and describes an apparatus that may be used to perform embodiments of the invention. While sub-headings are used in this section for organizational convenience, the disclosure of any particular feature (s) of the invention is/are not necessarily limited to any particular section or sub-section of this specification.

Process Overview

Figure 1:
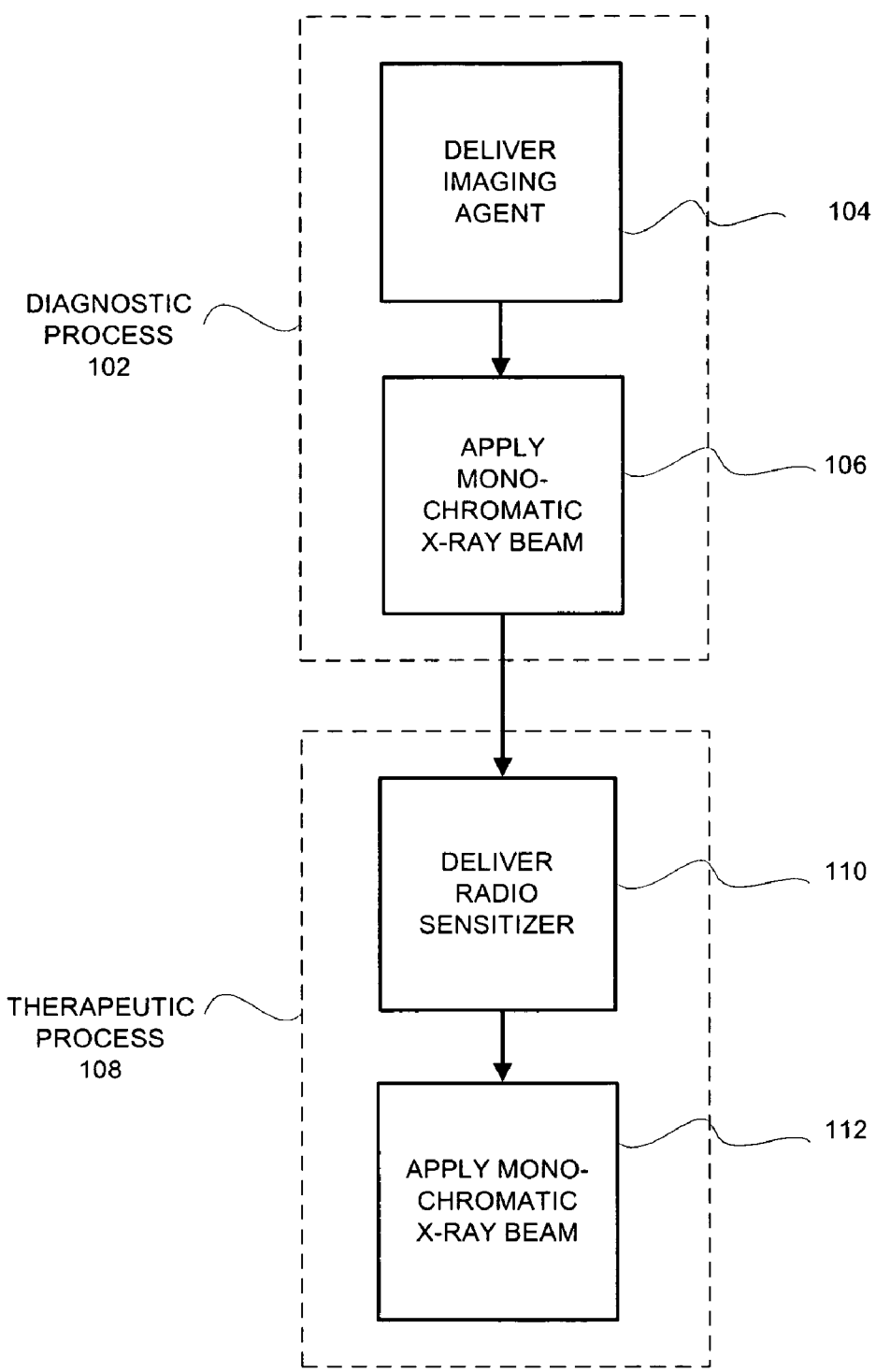
FIG. 1 is a process flow diagram of a diagnostic and therapeutic method, according to an embodiment of the invention.

FIG. 1 is a process flow diagram of a diagnostic and therapeutic method, according to an embodiment of the invention. As shown in FIG. 1, a diagnostic process 102 precedes a therapeutic process 108. The diagnostic process 102 begins at step 104. At step 104, an imaging agent is delivered; at step 106, a monochromatic x-ray beam is applied. Similarly, the therapeutic process 108 begins at step 110, where a radiosensitizer is delivered. Then, at step 112, a monochromatic x-ray beam is applied. Delivery of the imaging agent and radiosensitizer in steps 104 and 110, respectively, may be via oral consumption, injection, or other suitable method for causing accumulation in the target tissue.

In this embodiment of the invention, the same apparatus may be used for applying the monochromatic x-ray beam in steps 106 and 112. An advantage to such an implementation is that a patient need not be re-positioned between the diagnostic process 102 and the therapeutic process 108. This significantly reduces therapeutic targeting errors associated with the therapeutic process 108.

Alternative process embodiments are possible. For example, the diagnostic process can be performed without a subsequent therapeutic process. Moreover, the therapeutic process need not be preceded by the diagnostic process. In addition, with respect to diagnostic process 102, step 104 where an imaging agent is infused is optional and can be omitted. Likewise, with regard to therapeutic process 108, step 108 where a radiosensitizer is infused is optional and can be omitted; in one such embodiment, the imaging agent infused in step 104 is also used as a radiosensitizer in therapeutic process 108.

The diagnostic process 102 and the therapeutic process 108 are described in more detail below.

The Diagnostic Process

The manner in which an x-ray beam interacts with matter depends upon the chemical composition of the matter. Although the body is predominantly made up of hydrogen, oxygen, carbon, and nitrogen, the presence of tightly packed nuclear chromatin in highly cellular tumors, for example, results in a tissues' composition having less water, and therefore a different mass attenuation. So less hydrogen and oxygen is present in such tumors, and more phosphorous, nitrogen, and carbon in the DNA replaces them in the tissue. This increased amount of phosphorous, nitrogen and carbon increases the ability of the tissue to absorb x-rays.

In embodiments of the invention, x-ray absorption (and thus imaging contrast) can be improved by using a predetermined imaging agent in step 104 in combination with a tuned monochromatic x-ray beam in step 106. This exploits the naturally-occurring k-edge effects in the predetermined imaging agent. K-edge refers to the specific binding energy of the innermost or k-shell electron in the atom of interest, i.e. an atom within the predetermined imaging agent. Where, for example, iodine is introduced into a tissue in step 104 (e.g., by means of an iodine-tagged tumor-affinitive drug), the presence of iodine in rather small concentrations can be detected by applying monochromatic beam tuned to 33.2 keV (the binding energy of iodine's k-shell electron) in step 106 and using a suitable imaging detector.

Figure 2:
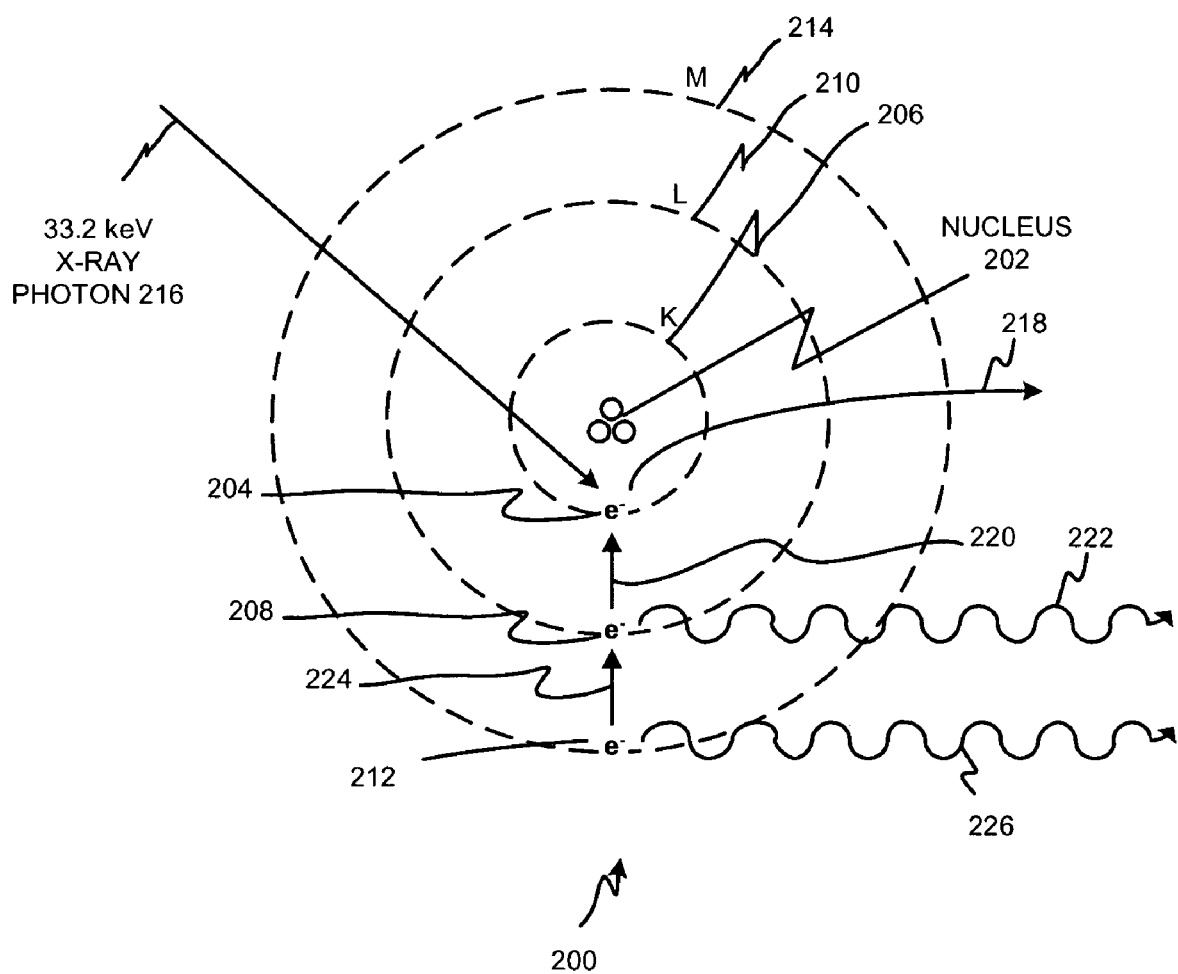
FIG. 2 is a schematic diagram of an iodine atom within an agent, according to an embodiment of the invention.

FIG. 2 is a schematic diagram of an iodine atom within an agent, according to an embodiment of the invention. As shown in FIG. 2, the atom 200 includes a nucleus 202, electrons 204 in orbitals in the k-shell 206, electrons 280 in orbitals in the l-shell 210, and electrons 212 in orbitals in the m-shell 214. When the energy of an x-ray photon 216 is tuned to match substantially the binding energy of the electrons 204 in orbitals in the k-shell 206, an electron 206 is displaced from its orbit (indicated by path 218). The x-ray photon 216, having transferred its energy to the electron 204, is absorbed, thus revealing the presence of the iodine in the original path of the x-ray photon 216.

FIG. 2 is simplified for purposes of clarity. Persons familiar with the modeling of atomic structure will appreciate that electrons move around the nucleus in orbitals, that each orbital can hold up to two electrons, that orbitals of the same subshell have the same shape and energy, and that each shell contains subshells of similar energy levels.

In other embodiments, the energy of x-ray photon 216 could be tuned to displace an electron in the l-shell or other shell. Moreover, in other embodiments, atoms other than iodine may be used in the imaging agent, as will be described below.

Various imaging agents may be suitable for use in step 104. These include standard iodinated x-ray contrast agents, Gadolinium magnetic resonance contrast agents, and compounds such as iodine-containing cyclooxygenase-2 (COX-2) agents, gadolinium (Gd)-containing immunoliposomes, and iodinated rose Bengal. COX-2 protein is not expressed extensively in normal cells, but is expressed significantly in stomach, colon, pancreas, liver, lung, breast, and prostate malignancies. This makes COX-2 an attractive molecular target in research animals and potentially humans. Researchers at other institutions have done preliminary work on diagnostic drugs such as: hepatocyte selective iodinated triglycerides, which act as a negative contrast agent; silver Mesotetra (4-sulfonatophenyl) porphyrine (AgTPPS4), which is a porphyrin derivative that accumulates in vasculature around tumors; iodine-containing micelles made from polymers; Gd compound P 760, which slowly diffuses into the interstitium; gases such as xenon (Xe) for airways and alveoli; perfluorocarbons which can be used as both liquids and gases; dextran-coated iron (Fe) oxide nanoparticles; and hexanuclear transition metal cluster compounds, to name a few.

There are various methods for infusing the imaging agent in step 104. For example, currently-available iodinated contrast agents are used intravenously, intra-arterially and even intrathecally. Moreover, because k-edge effects reduce the quantity of imaging agent that is required for improved imaging contrast, IV angiography using small intravenous injections is possible, reducing the need for catheterization of the arterial system.

Heavy elements do not necessarily need to be introduced exogenously into the body to take advantage of the k-edge effect. In other words, in some cases, step 104 may be omitted from diagnostic process 102. This is because some elements concentrate in tissues in certain diseases. For example: in Wilson's disease, abnormal over accumulation of copper (Cu) occurs; in hemochromatosis, iron builds up in tissues, such as liver and lung; lead poisoning affects calcium deposition and resorption in the regions of rapid bone growth at epiphyses. Any of these aforementioned elements can be detected with the application of a tuned monochromatic x-ray beam in step 106.

The monochromatic x-ray beam need not be exactly tuned to the k-edge of an element in step 106 to see an improvement in imaging contrast. In fact, at low concentrations of heavy elements (e.g., iodine), tissue concentrations at and beyond micromolar levels can be discerned when imaged far below the k-edge, due to the increased likelihood that lower energy x-ray photons will interact with heavier elements (more so than water) because of the photoelectric effect that is dominant in the 20-30 keV energy range, and because fluorescence x-rays can be detected emanating from smaller or thinner body parts.

The Therapeutic Process

According to embodiments of the invention, the therapeutic process 108 exploits a phenomenon known as Auger cascade (in combination with the k-edge effect described above with reference to diagnostic process 102). Auger cascade can be described with further reference to FIG. 2. When the k-shell electron 204 of the iodine atom 200 is displaced from its k-shell orbit 206 by the monochromatic x-ray photons 216 (tuned to 33.2 keV), the ejected electron 204 is replaced in the k-shell 206 by an electron 208 from the l-shell 210 (indicated by path 220). As the electron 208 drops from the l-shell 210 to the k-shell 206, it gives off a 28.3 keV characteristic photon 220. The electron 208 is then replaced in the l-shell 210 by an electron 212 from the m-shell 214 (indicated by path 224). In so doing, the electron 212 gives off a 4.3 keV photon 226. The n-shell (not shown) follows the lead of the other shells and contributes an electron to the m-shell 214, giving off a 0.6 keV photon (not shown). The sum of the energies of emitted photons is 33.2 keV.

Photons 220, 226, and the 0.6 keV photon (not shown) interact with matter in the surrounding medium, creating a cascade of Auger electrons traveling less than a few microns at most for the softer x-rays, but penetrating further for the more energetic ones. Thus, the Auger cascade phenomenon has the effect of releasing very large numbers of localized x-rays and electrons.

According to some embodiments of the invention, a radiosensitizer is infused in step 110 to enhance the therapeutic process 108. An example of an appropriate radiosensitizer is iodinated deoxyuridine (IUdR), which can be infused into a patient. IUdR replaces approximately 10% to 20% of the thymidine in the nuclear DNA of rapidly dividing cells. When the external monochromatic beam is applied in step 112 to displace the k-shell electron in the contained iodine, the Auger cascade effect described above occurs within the DNA, releasing localized x-rays and electrons creating double stranded breaks in the DNA. One Auger event in the DNA of a cell is the equivalent of delivering 0.05 gray (Gy) of radiation to the cell. As a result, the dose of external radiation needed for therapeutic process 108 is reduced. This reduction can be, for example, approximately 50% to 80% based on Monte Carlo simulations and laboratory experiments carried out in animals.

Figure 3A:
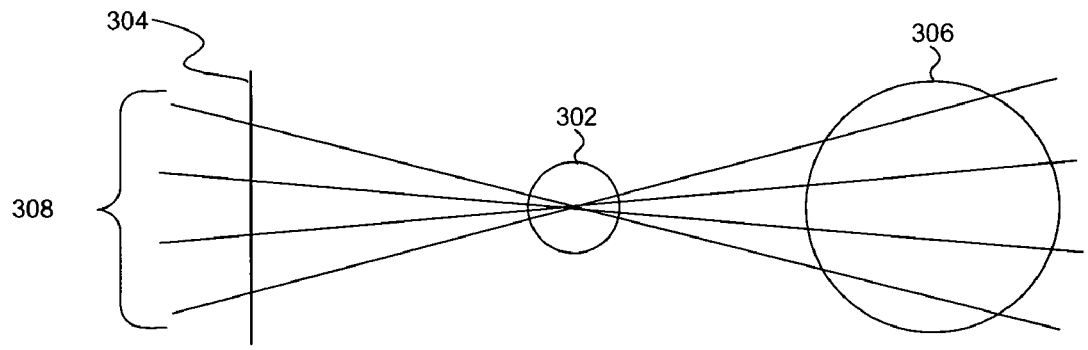
FIG. 3A is a schematic diagram of a known radiotherapy process.
Figure 3B:
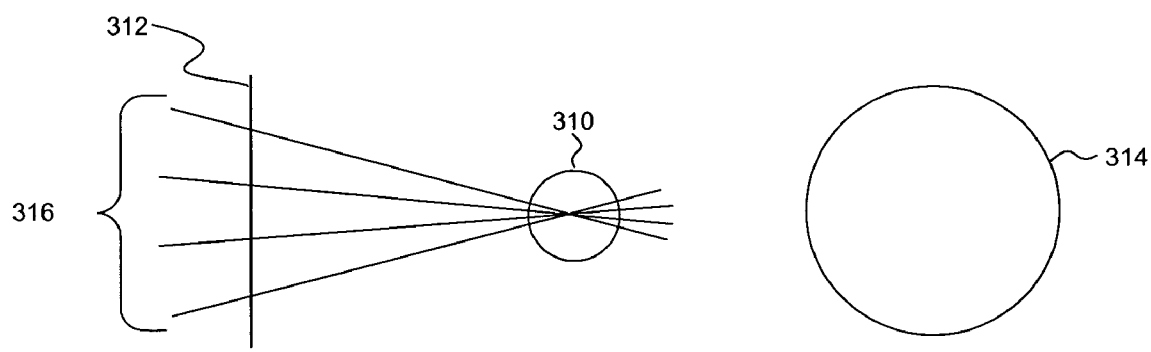
FIG. 3B is a schematic diagram of a monochromatic radiotherapy process without a radiosensitizer within the tumor, according to an embodiment of the invention.
Figure 3C:
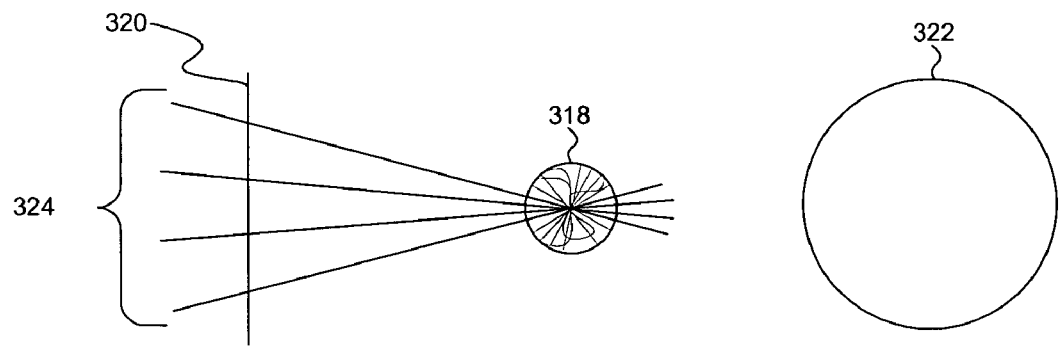
FIG. 3C is a schematic diagram of a monochromatic radiotherapy process with a radiosensitizer within the tumor, according to an embodiment of the invention.

FIGS. 3A-3C illustrate the advantages of therapeutic process 108. FIG. 3A is a schematic diagram of a known radiotherapy process. As shown in FIG. 3A, in known radiotherapy, external beam 308 passes through skin 304 towards target tissue 302. But because external beam 308 is at administered at a high energy level, surrounding tissue, including deep organ 306, is also exposed to the external beam 308.

FIG. 3B is a schematic diagram of a monochromatic radiotherapy process without a radiosensitizer within the tumor, according to an embodiment of the invention. In this embodiment, external beam 316 penetrates skin 312, towards target tissue 310. But because external beam 316 is low energy (e.g., in the range of 33.2 keV to 50 keV), radiation does not reach deep organ 314 (or it reaches deep organ 314 in much lower doses).

FIG. 3C is a schematic diagram of a monochromatic radiotherapy process with a radiosensitizer within the tumor, according to an embodiment of the invention. In the illustrated embodiment, a radiosensitizer is infused to collect in the target tissue. External beam 324 penetrates skin 320, towards target tissue 318. Because external beam 324 is low energy (e.g., in the range of 33.2 keV to 50 keV), radiation does not reach deep organ 322 (at least not in high doses). Moreover, because the external beam is tuned to approximately the energy level needed to displace a k-shell electron in the radiosensitizer, localized soft x-rays and electrons are released in the tumor 318 via the Auger cascade phenomenon, resulting in destruction of DNA and associated tumor cells. The presence of the radiosensitizer in the tumor also shields deeper tissues from the monochromatic beam to a great extent.

Alternative Embodiments

Various FDA-approved pharmaceuticals containing either iodine or gadolinium (Gd) exist and may be suitable for use as a radiosensitizer in step 110. These include products from the following categories: x-ray imaging agents, magnetic resonance imaging agents, radiodiagnostic agents, radiotherapy agents, thyroid-related products, antiseptics, disinfectants, expectorants, anti-amebics, anti-virals, anti-arrhythmics, and anti-neoplastics. Examples include: Amiodarone (an anti-arrhythmic), I-131 tositumomab (an anti-neoplastic), gemtuzumab (also an anti-neoplastic), I 131 sodium rose bengal (a diagnostic agent), and Iodoquinol (an anti-amebic).

It is possible that the combination of an adenovirus, a symporter gene, and tissue-specific compounds (such as prostate-specific compounds) can also be used in lieu of a radiosensitizer in step 110. While not containing the target atom itself, this combination, when given to mice, infects the prostate cells (or other targeted tissue), altering cellular genetic makeup, imparting new capabilities to the cell, and enabling the cell to transport and concentrate sodium iodide. Radioactive sodium iodide can then be infused into the patient and concentrated by the targeted cells.

Moreover, while experiments have used radioactive iodine uptake and its disintegrations to both diagnose and treat target tissue, collateral damage may be expected around the prostate cells themselves, and also in the thyroid gland, salivary glands, stomach and so forth where iodine may also accumulate. Use of non-radioactive iodine with an external beam tuned to the k-edge of the iodine could potentially spare these other organs, while still creating Auger cascades within the transformed cells to assist in the cell destruction.

In an alternative embodiment, aqueous polymer gels can be used to test distribution of dose in tissues to learn more about the k-edge enhancements with Auger cascade. Aqueous polymer gels comprise tissue-equivalent materials with radiosensitive monomers dispersed throughout the gel. The products of radiolysis (production of free radicals) cause the monomers to polymerize. The degree of polymerization depends directly upon radiation dose. When these gels are studied in a magnetic resonance imaging unit, the water relaxation times are shorter in the presence of polymers or macromolecules. The gels in essence act like self-developing three-dimensional photographic emulsions. By seeding target tissue containing k-edge drugs into these gels, the effectiveness can be tested and radiation dose equivalency can be studied using, for example, IUdR radiosensitizer and monochromatic radiation.

Apparatus

Figure 4:
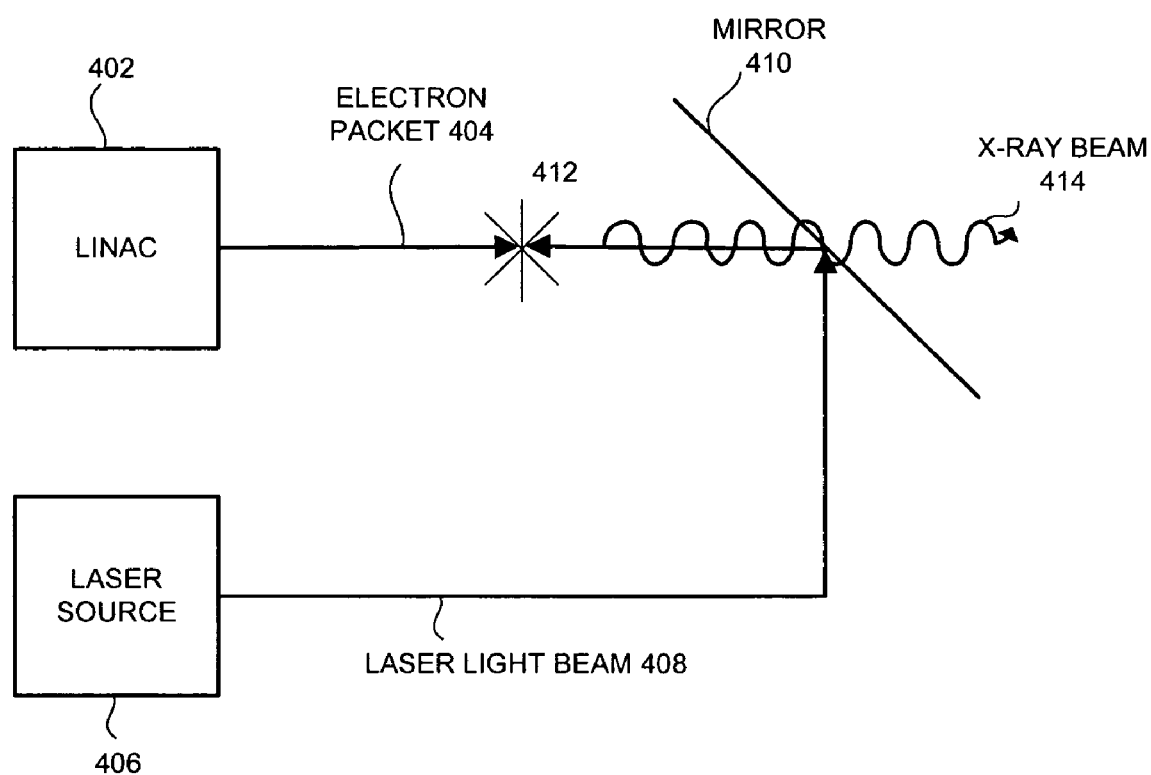
FIG. 4 is schematic diagram of system configured to generate a monochromatic x-ray beam, according to an embodiment of the invention.

FIG. 4 is a schematic diagram of system configured to generate a monochromatic x-ray beam, according to an embodiment of the invention. As shown in FIG. 4, a Linear Accelerator (LINAC) 402 produces an electron packet 404, and a laser source 406 produces a laser light beam 408. The laser light beam 408 is deflected off a mirror 410 causing an approximately head-on collision of electrons in the energetic electron packet 404 with photons in the laser light beam 408 at an interaction zone (IZ) 412. Mirror 410 can be, for example, a beryllium surface. The photons in the laser light beam 408 scatter off the electrons in the electron packet 404, gaining energy and shortening their wavelength to the x-ray region of the spectrum.

Since the photons are giving off energy while in motion, the system can be said to produce x-ray photons via inverse Compton scattering. In addition, because the resulting low-energy photons in x-ray beam 414 move in a direction opposite the laser light beam 408 (and nearly collinear with the direction of electron packet 404) the system illustrated in FIG. 4 can be said to produce x-ray photons via Compton backscattering.

Because the energy of the electron packets 404 is tunable, the resulting x-rays are tunable. Moreover, because the laser light beam is at a constant wavelength, the resulting x-rays are substantially monochromatic. The tunable monochromatic x-ray beam 414 is generated in approximately the same direction as the original electron packets 404, passing through the mirror 410.

As described above, one advantage of a tunable energy range is that k-edge and Auger cascade effects can be exploited for many different atomic species. An advantage of a tunable frequency in the x-ray beam is that different tissues more readily absorb radiation at different frequencies. Thus, the apparatus used in embodiments of the invention can be adjusted in energy pulse length and quantity of photons, as desired.

The disclosures of U.S. Pat. Nos. 6,332,017 and 6,687,333, each incorporated by reference in their entirety, provide additional description of embodiments of the apparatus illustrated in FIG. 4 for producing tunable monochromatic x-rays. U.S. Pat. No. 6,693,931, also incorporated by reference in its entirety, discloses a system and method for stabilizing the phase of the x-rays beam by synchronizing the LINAC 402 with the laser source 406. A representative apparatus has been constructed that delivers $10^{10}$ x-ray photons/8 ps pulse throughout a tunable range of 12-50 keV at a 1-10% bandwidth in a cone beam area geometry.

Conclusion

Embodiments of the invention thus provide, among other things, methods for improving x-ray imaging contrast, reducing the amount of energy needed for effective external beam radiation, and substantially limiting alignment errors between diagnostic and therapeutic processes. Those skilled in the art can readily recognize that numerous variations and substitutions may be made in the invention, its use and its configuration to achieve substantially the same results as achieved by the embodiments described herein. Accordingly, there is no intention to limit the invention to the disclosed examples. Many variations, modifications and alternative constructions fall within the scope and spirit of the disclosed invention as expressed in the claims. For example, alternative imaging and/or therapeutic agents may be used with the tuned external beam radiation. In addition, although references are made to embodiments of the invention, all embodiments disclosed herein need not be separate embodiments. In other words, many of the features disclosed herein can be utilized in combinations not expressly illustrated.

What is claimed is:

1. A method comprising:
   accumulating an agent in a target tissue;
   applying an external substantially monochromatic x-ray beam to the target tissue, the external substantially monochromatic x-ray beam being tuned approximately to a binding energy level of an electron shell in an atom of the agent; and
   imaging based on and destroying the target tissue with the substantially monochromatic x-ray beam.

2. The method of claim 1, wherein the accumulating includes delivering at least one of iodine, gadolinium, silver, gold, or platinum.

3. The method of claim 1, wherein accumulating includes delivering a transporter of the agent.

4. The method of claim 3, wherein the transporter of the agent is selected from the group of x-ray imaging agents, magnetic resonance imaging agents, radioactive agents, radiotherapy agents, thyroid-related products, antiseptics, disinfectants, expectorants, anti-amebics, anti-virals, anti-arrhythmics, or anti-neoplastics.

5. The method of claim 3, wherein the transporter of the agent includes a pharmaceutical having heavy elements, the heavy elements replacing or being accumulated in a portion of DNA in the target tissue in response to the accumulating, the DNA breaking in response to the applying.

6. The method of claim 5, further comprising imaging the target tissue before the accumulating and the applying.

7. The method of claim 1, further comprising tuning the external substantially monochromatic x-ray beam to a predetermined frequency associated with an x-ray absorption property of the target tissue after the accumulating and prior to the applying.

8. The method of claim 1, wherein the electron shell is one of a k-shell, an l-shell, and a m-shell.

9. The method of claim 1, wherein the applying includes producing the substantially monochromatic x-ray beam via inverse Compton scattering.

10. A method comprising:
accumulating an agent in DNA of a target tissue;
imaging the target tissue based on a first substantially monochromatic x-ray beam during a first period;
tuning a second substantially monochromatic x-ray beam to approximately a K-edge associated with the agent at a location of the target tissue; and
externally applying the tuned substantially monochromatic x-ray beam to the target tissue during a second period, a first portion of the DNA of the target tissue breaking from a second portion of the DNA of the target tissue in response to the applying, the second period having at least a portion overlapping with the first period.

11. The method of claim 10, wherein the accumulating includes delivering a pharmaceutical having heavy elements.

12. The method of claim 10, wherein the accumulating includes:
delivering a combination of an adenovirus, a symporter gene, a tissue-specific compound; and,
delivering radioactive sodium iodide.

13. The method of claim 10, wherein the applying includes producing the substantially monochromatic x-ray beam via inverse Compton scattering.

14. The method of claim 10, the applying causing an Auger cascade in the target tissue.

15. A method for performing diagnosis and therapy, comprising:
delivering a first agent in a target tissue;
imaging, after the delivering, the target tissue based on an external substantially monochromatic x-ray beam; and
destroying, after the delivering, cells of the target tissue with the substantially monochromatic x-ray beam.

16. The method of claim 15, wherein the external substantially monochromatic x-ray beam being tuned to approximately a K-edge associated with the first agent.

17. The method of claim 15, further comprising delivering a second agent after the imaging and before the destroying, the first agent being an imaging agent, the second agent being a radiosensitizer.

18. The method of claim 15, wherein the destroying is based on an Auger cascade effect in the target tissue.

19. The method of claim 15, the imaging and the destroying including producing the external substantially monochromatic x-ray beam via inverse Compton scattering.

20. The method of claim 15, further comprising:
delivering a second agent after the imaging and before the destroying, the first agent being an imaging agent, the second agent being a combination of an adenovirus, a symporter gene, a tissue-specific compound; and
delivering a third agent after delivering the second agent and before the destroying, the third agent being sodium iodide.

21. A method, comprising:
imaging a target tissue based on an external substantially monochromatic x-ray beam during a first time period; and destroying cells of the target tissue with an external substantially monochromatic x-ray beam during a second time period having at least a portion overlapping with the first time period.

22. The method of claim 21, wherein the external substantially monochromatic x-ray beam associated with the imaging substantially corresponds to the external substantially monochromatic x-ray beam associated with destroying.

23. The method of claim 21, wherein the external substantially monochromatic x-ray beam associated with the imaging differs from the external substantially monochromatic x-ray beam associated with destroying.

24. The method of claim 21, wherein the external substantially monochromatic x-ray beam associated with the imaging is tuned to an energy level less than 4 MeV.

25. The method of claim 21, wherein the external substantially monochromatic x-ray beam associated with the destroying is tuned to an energy level less than 4 MeV.

26. The method of claim 21, further comprising:
delivering an agent in a target tissue, the external substantially monochromatic x-ray beam associated with the imaging is tuned to approximately a K-edge associated with the agent.

27. The method of claim 21, further comprising:
delivering an agent in a target tissue, the external substantially monochromatic x-ray beam associated with the destroying is tuned to approximately a K-edge associated with the agent.

28. An apparatus, comprising:
a laser source; and
a tunable electron beam source coupled to the laser source, the tunable electronic beam source and the laser source collectively configured to produce a substantially monochromatic x-ray beam tuned to approximately a binding energy level of an electron shell in an atom of an agent associated with target tissue,
the substantially monochromatic x-ray beam being configured such that the target tissue is imaged based on and destroyed with the substantially monochromatic x-ray beam.

29. The apparatus of claim 28, wherein:
the substantially monochromatic x-ray beam is configured such that the target tissue is imaged during a first time period and destroyed based on the substantially monochromatic x-ray beam during a second time period having at least a portion overlapping with the first time period.

30. The apparatus of claim 28, wherein:
the substantially monochromatic x-ray beam is a first substantially monochromatic x-ray beam and configured such that the target tissue is imaged based on the first substantially monochromatic x-ray beam,
the tunable electronic beam source and the laser source is collectively configured to produce a second substantially monochromatic x-ray beam configured to destroy cells of the target tissue.

31. An apparatus, comprising:
a laser source; and
a tunable electron beam source coupled to the laser source, the tunable electronic beam source and the laser source collectively configured to produce a substantially monochromatic x-ray beam tuned to approximately a binding energy level of an electron shell in an atom of an agent associated with target tissue,
the substantially monochromatic x-ray beam is a first substantially monochromatic x-ray beam and configured such that the target tissue is imaged based on the first substantially monochromatic x-ray beam during a first period, the tunable electronic beam source and the laser source are collectively configured to produce a second substantially monochromatic x-ray beam configured to destroy cells of the target tissue during a second period having at least a portion overlapping with the first period.

32. The apparatus of claim 28, wherein the tunable electronic beam source and the laser source collectively are configured to produce the substantially monochromatic x-ray beam tuned an energy level less than 4 MeV.

33. The apparatus of claim 28, wherein the electron shell is one of a k-shell, an l-shell, and a m-shell.

34. The apparatus of claim 28, wherein the agent includes a pharmaceutical having heavy elements configured to replace or being accumulated in a portion of DNA in the target tissue, the substantially monochromatic x-ray beam configured to break the DNA.

* * * * *